United States Patent [19]

Fukuma et al.

[11] Patent Number: 4,796,989
[45] Date of Patent: Jan. 10, 1989

[54] OPTHALMOLOGICAL MEASURING APPARATUS

[75] Inventors: Yasufumi Fukuma; Yoshinori Oana; Akihiro Arai, all of Tokyo, Japan

[73] Assignee: Tokyo Kogaku Kikai Kabushiki Kaisha, Tokyo, Japan

[21] Appl. No.: 73,707

[22] Filed: Jul. 15, 1987

[30] Foreign Application Priority Data

Jul. 17, 1986 [JP] Japan .................................. 61-168825

[51] Int. Cl.⁴ .............................................. A61B 3/10
[52] U.S. Cl. .................................... 351/212; 351/205
[58] Field of Search ............... 351/205, 211, 212, 237, 351/208

[56] References Cited

U.S. PATENT DOCUMENTS 4,572,628 2/1986 Nohda .................................. 351/212

FOREIGN PATENT DOCUMENTS 58-29446 2/1983 Japan .

Primary Examiner—Rodney B. Bovernick
Assistant Examiner—P. M. Dzierzynski
Attorney, Agent, or Firm—Finnegan, Henderson, Farabow, Garrett & Dunner

[57] ABSTRACT

An ophthalmological measuring apparatus is disclosed. It comprises a projecting systems for projecting a target image to the cornea and retina of an eye to be tested, respectively, a measuring optical system for being introduced a corneal reflecting beam of light and a retina reflecting beam of light from the eye, a light receiving portion for receiving the corneal reflecting beam of light and the retina reflecting beam of light through the measuring optical system and photoelectrically transferring the same, an image displaying device for displaying an image of the anterior portion of the eye based on a signal from the light receiving portion, and a calculating device for calculating and measuring a corneal configuration and an eye refractive power of the eye to be tested based on the signals of the corneal reflecting beam of light and the retina reflecting beam of light detected by the light receiving portion.

4 Claims, 4 Drawing Sheets

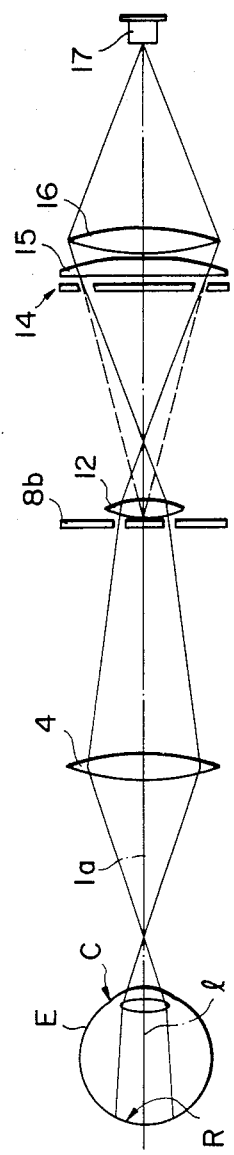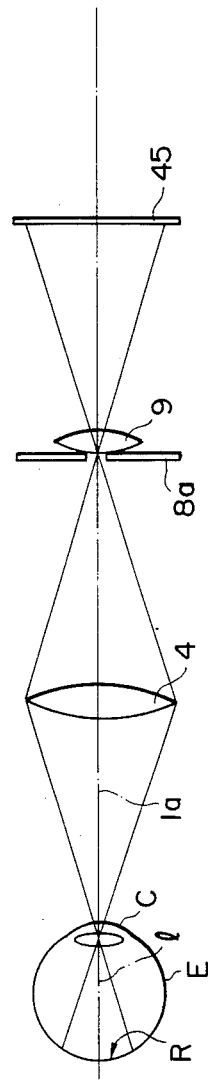

OPTHALMOLOGICAL MEASURING APPARATUS

BACKGROUND OF THE INVENTION

This invention relates to an ophthalmological measuring apparatus for measuring a corneal configuration, an eye refractive power, etc. of an eye to be tested.

A conventional ophthalmological measuring apparatus for measuring a corneal configuration, an eye refractive power, etc. of an eye to be tested is of the type that a target image is projected to the cornea and the retina of an eye to be tested respectively, a corneal reflecting image and a retina reflecting image of the eye are projected to a light receiving means having a photoelectric transfer characteristic through a measuring optical means, and based on a signal detected by the light receiving means, the corneal configuration and the refractive power of the eye to be tested are calculated and measured.

In this conventional apparatus, the alignment between the eye to be tested and the measuring optical means is required to be verified prior to the measurement. For this purpose, an image pick-up tube is separately provided in addition to a provision of the light receiving means adapted to use for the measurement in order to observe the anterior portion of the eye to be tested, and the eye to be tested and the measuring optical means are aligned by the image of the anterior portion which is shown on a TV monitor by the signal from the image pick-up tube.

However, the conventional apparatus has the shortcoming in that since an image pick-up tube for observing the anterior portion is separately provided in addition to a provision of a light receiving means adapted to use for the measurement, more component parts are required to that extent. In addition, a space for forming an optical path for introducing a beam of light to the image pick-up tube is required to be provided in the ophthalmological measuring apparatus in order to form an image of the anterior portion. Accordingly, the ophthalmological measuring apparatus cannot be made compact as a whole.

SUMMARY OF THE INVENTON

The present invention was accomplished in order to overcome the above-mentioned problems. It is therefore a general object of the present invention to provide an ophthalmological measuring apparatus, in which a smaller number of component parts are required compared with the conventional apparatus and which can be made more compact compared with the conventional apparatus.

To achieve the above object, there is essentially provided an ophthalmological measuring apparatus comprising a projecting means for projecting a target image to the cornea and retina of an eye to be tested, respectively, a measuring optical means for being introduced a corneal reflecting beam of light and a retina reflecting beam of light from the eye, a light receiving means for receiving the corneal reflecting beam of light and the retina reflecting beam of light through the measuring optical means and photoelectrically transferring the same, an image displayer for displaying an image of the anterior portion of the eye based on a signal from the light receiving means, and a calculating means for calculating and measuring a corneal configuration and an eye refractive power of the eye to be tested based on the signals of the corneal reflecting beam of light and the retina reflecting beam of light detected by the light receiving means.

According to an ophthalmological measuring apparatus of the present invention, when an image of the anterior portion of an eye to be tested is projected to a light receiving means through a measuring optical means, the image of the anterior portion is transferred into a detecting signal by the light receiving means and is displayed on an image displayer. Accordingly, it is possible to verify the alignment between the measuring optical means and the eye to be tested while observing the image displayed on the displayer. When the alignment between the eye and the measuring optical means has been verified, a target image is projected to the cornea and retina of the eye to be tested, respectively. Based on a signal from the light receiving means, the measurement of the corneal configuration and the eye refractive power is started.

BRIEF DESCRIPTION OF THE DRAWINGS

The above and other objects, features and advantages of the present invention will become more apparent from the following detailed description of a preferred embodiment taken in conjunction with the accompanying drawings, in which:

FIGS. 2 and 3 are schematic views for explaining a conic prism, a ring pattern, and a ring diaphragm which are adapted to form a target image of the retina, and which are employed in the above embodiment;

FIG. 4 is a schematic view for explaining how a retina reflecting image is projected to a light receiving means according to the embodiment;

DETAILED DESCRIPTION OF THE PREFERRED EMBODIMENT

One preferred embodiment of an ophthalmological measuring apparatus according to the present invention will be described hereunder with reference to the accompanying drawings.

Figure 1:
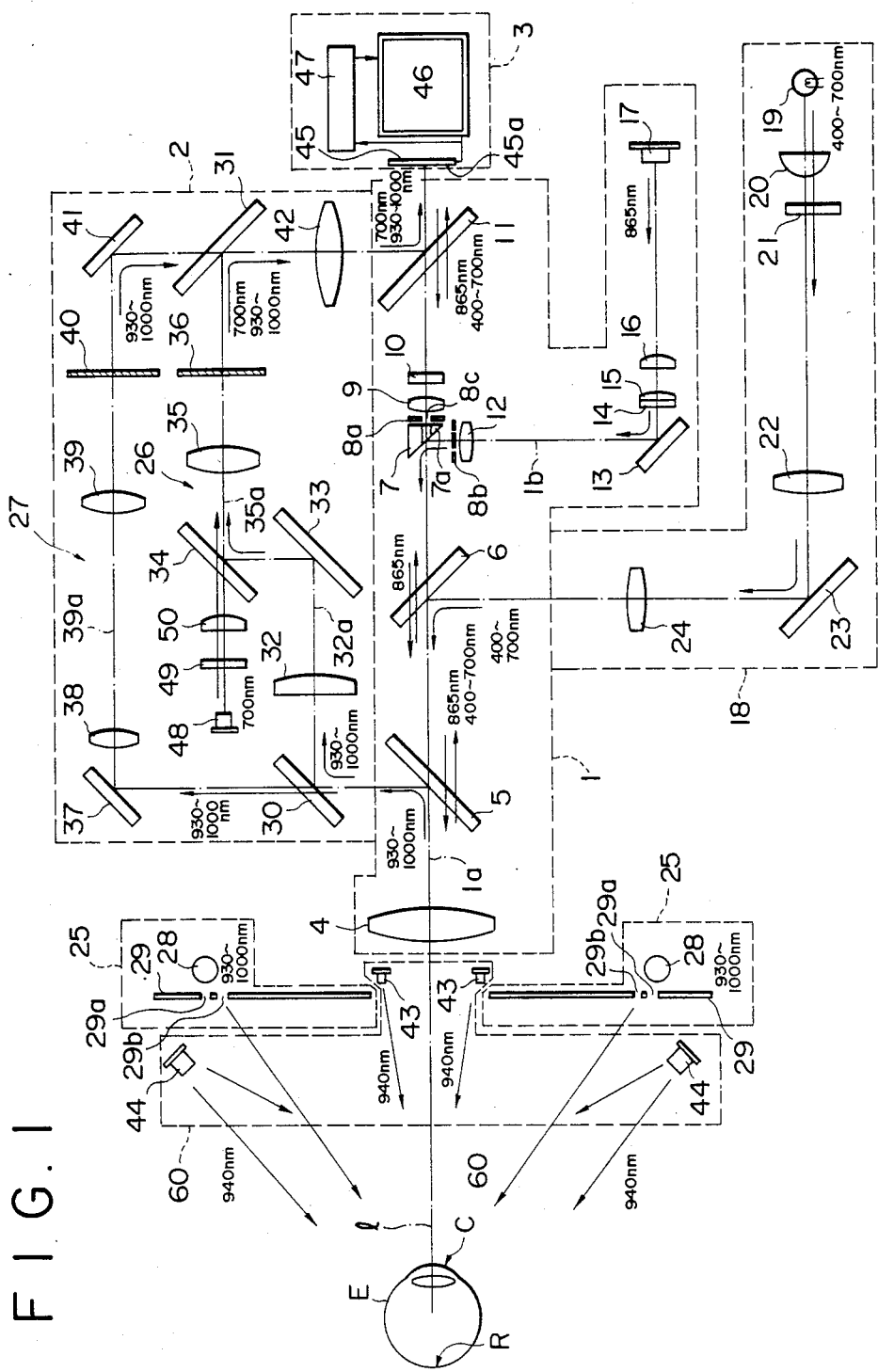
FIG. 1 is a schematic view showing the constitution of an ophthalmological measuring apparatus according to one embodiment of the present invention.
Figure 6:
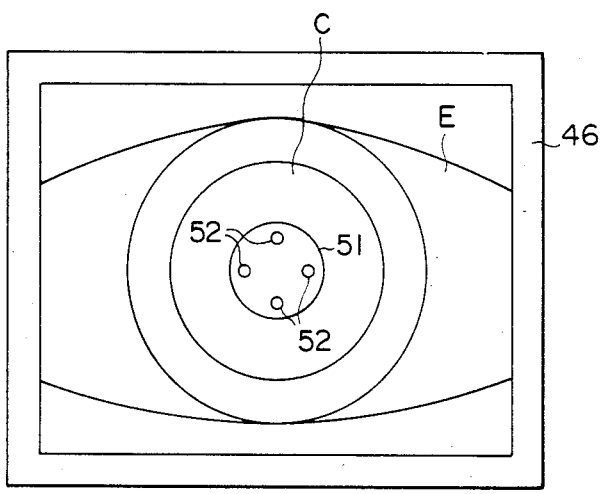
FIG. 6 is a schematic view showing the state of an image of the anterior portion of an eye to be tested when the alignment has been verified.

This ophthalmological measuring apparatus, as is shown in FIG. 1, comprises an eye refractive power measuring optical means 1, a corneal configuration optical means 2, and a light receiving means 3. In order to verify the alignment, the optical axis 1a of the eye refractive power measuring optical means 1, as is shown in FIG. 6, is held in alignment with the center 1 of the pupil (not shown) of an eye E to be tested, and the eye E and the eye refractive power measuring optical means 1 are separated at a predetermined space.

The eye refractive power measuring optical means 1 comprises an objective lens 4 disposed adjacent to the eye E, a half mirror 5, a half mirror 6, a perforated reflecting prism 7, an annular diaphragm 8a, a relaying lens 9, a filter 10, a half mirror 11, a ring diaphragm 8b, a relaying lens 12, a reflecting mirror 13, a ring pattern 14, a conic prism 15, a condenser lens 16, and an LED 17.

The optical axis 1a of the eye refractive power measuring optical means 1 is commonly used by the objective lens 4. The half mirror 5, the half mirror 6, the perforated reflecting prism 7, the conic diaphragm 8a, the relaying lens 9, the filter 10, and the half mirror 11 are arranged on the optical axis 1a. The ring diaphragm 8b, the relaying lens 12, the reflecting mirror 13, the ring pattern 14, the conic prism 15, the condenser lens 16, and the LED 17 are arranged on the optical axis 1b which is diversified from the optical axis 1a by the perforated reflecting prism 7.

The half mirror 5 functioning as an optical path diversifying means, has such a characteristic as to permit light of a wavelength of from 400 to 700 nm and about 865 nm to transmit therethrough and reflect light of a wavelength of from 910 to 1000 nm.

The half mirror 6 functioning as a first optical path composing means, has such a characteristic as to reflect light of a wavelength of from 400 to 700 nm and permit light of a wavelength of 865 nm to transmit therethrough. The half mirror 6 has such a function as to reflect a fixation mark image from a fixation mark image projecting optical means 18 adapted to form a fixation mark image towards the objective lens 4. The fixation mark image projecting optical means 18 is adapted to fix the gazing direction of the eye E and comprises a tungsten light source 19 for emitting a visible light of a wavelength of from 400 to 700 nm, a condenser lens 20, a fixation mark 21, a collimating lens 22, a reflecting mirror 23, and a relaying lens 24. A visible light of a wavelength of from 400 to 700 nm emitted from the tungsten light source 19 is radiated to the fixation mark 21 through the condenser lens 20. A beam of light from this fixation mark 21 is introduced to the half mirror 6 by the collimating lens 22, the reflecting mirror 23, and the relaying lens 24 and is then reflected by the half mirror 6. The beam of light reflected by the half mirror 6 is projected to the retina R of the eye E by the objective lens 4.

Figure 2:
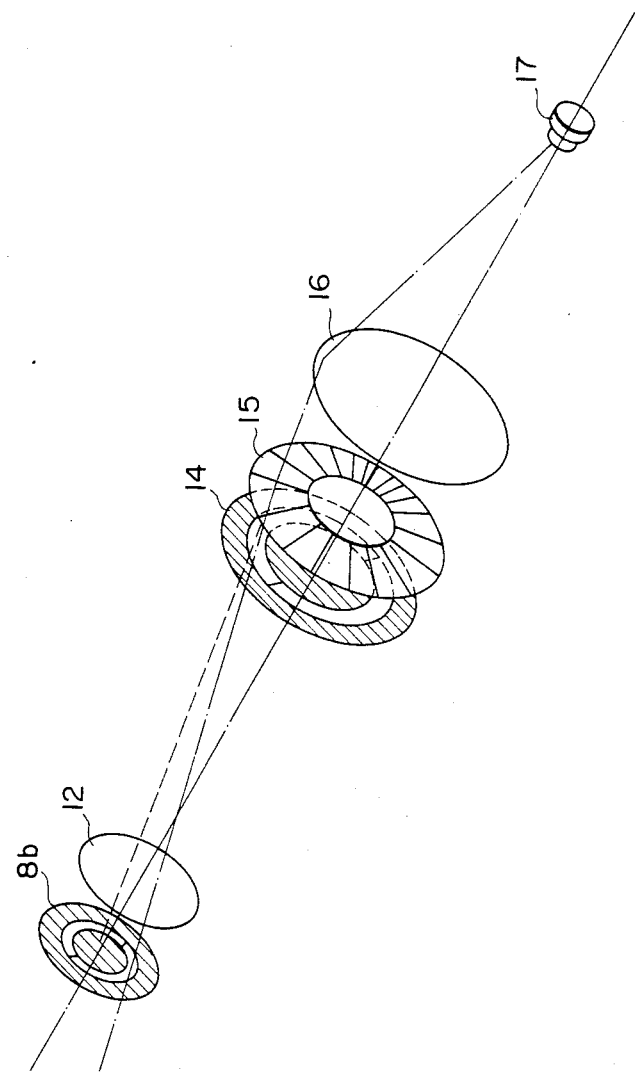

The perforated reflecting prism 7 is adapted to reflect light of a wavelength of about 865 nm emitted from the LED 17 as a luminous light source for measuring the eye refractive power towards the eye E and introduce light reflected by the retina R of the eye E to the light receiving means 3. The ring diaphragm 8b is disposed adjacent to the perforated reflecting prism 7. When a retina beam of light is projected to the perforated reflecting prism 7, the retina beam of light is reflected towards the eye E by the perforated reflecting prism 7. Regarding this retina beam of light, as is shown in FIGS. 2 and 3, the light emitted from the LED 17 is condensed by the condenser lens 16, is polarized by the conic prism 15, is further condensed by the ring pattern 14 and the relaying lens 12, and is thereafter formed into a retina target image as a ring pattern image on the retina R of the eye E by the ring diaphragm 8b and the objective lens 4. The perforated reflecting prism 7 is provided with a through hole 7a extending along the optical axis 1a. After condensed by the objective lens 4, the retina reflecting beam of light of the retina target image which was formed on the retina R of the E is permitted to pass through the through hole 7a.

The annular diaphragm 8a is provided with a through hole 8c communicating with the hole 7a of the perforated reflecting prism 7. As is shown in FIG. 4, the retina reflecting beam of light condensed by the objective lens 4 is contracted by this hole 8c and is introduced to the filter 10 by the relaying lens 9. A retina reflecting target image as a ring-shaped pattern image is formed on the area CCD 45 by the half mirror 11.

The filter 10 has such a characteristic as to permit only light of a wavelength of about 865 nm to transmit therethrough. Thus, the filter 10 permits the retina reflecting beam of light which transmits the annular diaphragm 8a is permitted to transmit therethrough and introduces the beam of light to the half mirror 11. The half mirror 11 as a second optical path composing means has such a characteristic as to permit light of a wavelength of about 865 nm to transmit therethrough, and to reflect light of a wavelength of from 930 to 1000 nm so that the light is projected to the light receiving means 3.

The corneal configuration measuring optical means 2 comprises a corneal target image projecting means 25 for projecting a corneal target image for measuring the corneal configuration to the cornea C, a low power optical means 26 for forming the corneal reflecting target image on the area CCD 45, and a high power optical means 27.

The corneal target image projecting means 25 comprises a xenon lamp 28 for emitting light of a wavelength of from 930 to 1000 nm, and a slit plate 29 for making the light from the xenon lamp 28 into a ring-shaped corneal target image. The xenon lamp 28 is provided in a ring shape about the optical axis 1a. The slit plate 29 is provided with a ring-shaped slit hole 29a about the optical axis 1a. When the light of a wavelength of from 930 to 1000 nm from the xenon lamp 28 is radiated to the slit plate 29, this light is made into a ring light by the slit holes 29a and 29b and is projected to the cornea C of the eye E as a corneal target image. The corneal target image which is to be projected to the cornea C is reflected by the outer surface of the cornea C, and is introduced to the low power optical means 26 and the high power optical means 27 by the objective lens 4 and the half mirror 5, and a ring-shaped cornea reflecting image is formed on the area CCD 45 by both the optical means 26 and 27.

The low power optical means 26 and the high power optical means 27 are separated from the optical path of the retina reflecting image by the half mirror 5 and is superposed with the optical path of the corneal reflecting image by the half mirror 11. A half mirror 30 opposite the half mirror 5 is tranparent with respect to light of a wavelength of from 930 to 1000 nm. The low power optical means 26 and the high power optical means 27 are separated the optical paths by the half mirror 30 with each other, and the optical paths are superposed again by a half mirror 31 opposite the half mirror 11.

The low power optical means 26 comprises a relaying lens 32, a reflecting mirror 33, a half mirror 34, a low power lens 35, and a shutter 36. The half mirror 30 and the reflecting mirror 33 are provided on the optical axis 32a of the relaying lens 32. The half mirror 34 is provided at a position opposite the reflecting mirror 33. The half mirrors 31 and 34 are provided on the optical axis 35a of the low power lens 35. An LED 48, a collimating scale plate 49, and a collimater lens 50 are provided behind (i.e., opposite side of the low power lens 35) of the half mirror 34. An image of a collimating scale (for example, a ring pattern) provided at the collimating scale plate 49 is projected on the area CCD 45 by the low power lens 35 and the relaying lens 42. The light emitted from the LED 48 is about 700 nm in wavelength. The half mirror 34 has such a characteristic as to permit a collimating scale light of a wavelength of about 700 nm to transmit therethrough and reflect a corneal reflecting image of a wavelength of from 930 to 1000 nm. The shutter 36 is a liquid crystal shutter.

The high power optical means 27 comprises a reflecting mirror 37, a relaying lens 38, a high power lens 39, a shutter 40, and a reflecting mirror 41. The reflecting mirror 37, the relaying lens 38, the shutter 40, and the reflecting mirror 41 are provided on the optical axis 39a of the high power lens 39. The reflecting mirror 37 is placed opposite the half mirror 30. The reflecting mirror 37 reflects a corneal reflecting image from the half mirror 30 and introduces the same to the high power lens 39 through the relaying lens 38. The reflecting mirror 41 is placed opposite the half mirror 31 and projects a corneal reflecting image which is varied by the power of the objective lens 4, the relaying lens 38 and the high power lens 39 to the half mirror 11 through the half mirror 31 and the relaying lens 42. The shutter 40 is a liquid crystal shutter and can be switched with the shutter 36 of the low power optical means 26. The corneal reflecting image from the cornea can be blocked in turn at the low power optical means 26 and the high power optical means 27 by means of switching operation of the shutters 36 and 40.

A light source portion 60 for verifying the alignment between the objective lens 4 and the eye E is provided at the objective lens 4 side of the eye refractive power measuring optical means 1.

The light source portion 60 for verifying the alignment comprises an LED 44 for emitting light of a wavelength of about 940 nm for illuminating the anterior portion, and an LED 43 for emitting spot light of a wavelength of about 940 nm. The LED 44 is provided in pair in vertical relation with the optical axis 1a of the eye refractive power measuring optical means 1 serving as a symmetical axis, while the LED 43 is provided four in number adjacent to the eye E.

The LEDs 44 and 43, the xenon lamp 28 and the slit plate 29 are integrally provided with the measuring optical means. A collimating spot light for verifying the alignment of the objective lens 4 with respect to the eye E is emitted from the LED 43. The collimating spot light for verifying the alignment emitted from the LED 43 is introduced to the low power optical means 26 and the high power optical means 27 together with the corneal reflecting image. The light which was introduced to the low power optical means 26 is used in order to verify the alignment.

Figure 5:
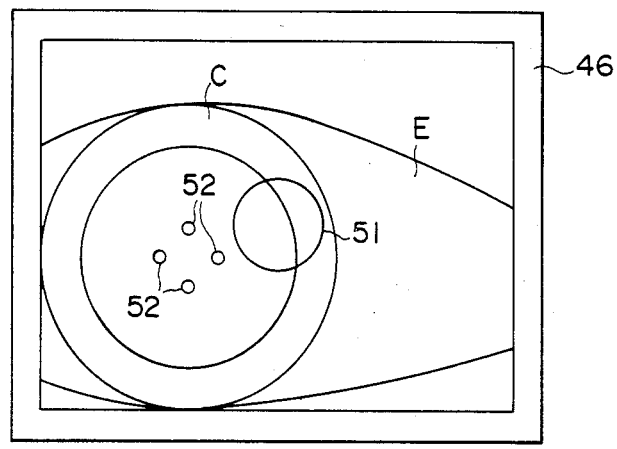
FIG. 5 is a schematic view for showing the state of an image of the anterior portion of an eye to be tested which is displayed on a TV monitor during verification of the alignment.

The light receiving means 3 comprises an area CCD 45 as a light receiving means capable of a photoelectric transfer, a TV monitor 46 as an image displayer, and a calculating apparatus 47. The area CCD 45 outputs an image signal corresponding to an image formed on the front surface 45a thereof to the TV monitor 46 and the calculating apparatus 47. With this constitution, the LEDs 44, 43 and 48 are lighted up prior to the measurement, and at the same time the shutter 36 is opened and the shutter 40 is shut. An anterior portion image of the eye E is projected on the area CCD 45 in superposed relation with the cornea reflecting image and the collimating scale image of the collimating spot light by the low power optical means 26. The image signals of these images are transmitted to the TV monitor 46 and are displayed thereon as visible images. FIGS. 5 and 6 illustrate the screen of the TV monitor 46 at that time, wherein 52 denotes a collimating spot image formed by the corneal reflecting of the eye E, 51 denotes a collimating scale image, and C denotes an anterior portion image of the eye E. FIG. 6 illustrates a state of the whole apparatus which were moved from the state of FIG. 5 and in which the alignment has been verified. In this way, the alignment can be easily verified collimating the images on the TV monitor prior to the measurement.

When the xenon lamp 28 is lighted up after the alignment has been verified, first, an outer ring-shaped corneal reflecting image is projected to the area CCD 45 by the low power optical means 26 through the objective lens 4, the half mirror 5, the corneal configuration measuring optical means 2, and the half mirror 11. Thereafter, an inner ring-shaped corneal reflecting image is projected by the high power optical means 27. Then, image signals of these corneal reflecting images are transmitted to the calculating apparatus 47, and the sizes and shapes of the rings are calculated there based on the respective image signals. A measuring result regarding the corneal configuration of the eye E corresponding to this result is displayed on the TV monitor 46.

When the LED 17 is lighted up and the retina target image is projected to the retina R after the corneal configuration has been measured, the ring-shaped retina reflecting image reflected by the retina R is projected to the area CCD 45 through the eye refractive power measuring optical means 1, an image signal of the retina reflecting image is transmitted to the calculating apparatus 47, the size and shape of the ring is calculated there based on this image signal, and a measuring result regarding the eye refractive power of the eye E corresponding to this result is displayed on the TV monitor 46.

As described in the foregoing, according to an ophthalmological measuring apparatus of the present invention, an image displayer is provided at a light receiving means which is used both for a corneal configuration measurement and a retina refractive power measurement, and an image of the anterior portion is displayed by the image displayer. Accordingly, observation of the image of the anterior portion during the alignment verification, and corneal configuration measurement and eye refractive power measurement after the alignment verification can be performed by the same light receiving means, respectively. Thus, component parts can be reduced in number compared with the conventional apparatus. In addition, an ophthalmological measuring apparatus can be made compact as a whole.

It will be appreciated that various changes and modifications of the preferred embodiments, some of which have been described above, may be made without departing from the spirit and the scope of the present invention as defined in the accompanying claims.

What is claimed is:

1. An ophthalmological measuring apparatus comprising:
   (A) projecting means for projecting first and second target images to the retina and cornea of an eye to be tested, respectively;
   (B) anterior portion illuminating means for providing illumination to an anterior portion of the eye;
   (C) measuring optical means including:
      (1) eye refractive power measuring optical means for forming a retina reflected beam of light from said first target image reflected by said retina and projecting said retina reflected beam of light along a first optical path;

(2) corneal configuration measuring optical means for forming a cornea reflected beam of light from said second target image reflected by said cornea and projecting said cornea reflected beam of light along a second optical path; and (3) anterior portion reflection means for forming an anterior portion reflected beam of light from said illumination reflected by said anterior portion of the eye;

(D) light receiving means for receiving the corneal reflected beam of light, the retina reflected beam of light and the anterior portion reflected beam of light through said measuring optical means at a light receiving surface and generating a cornea image signal, a retina image signal, and an anterior portion image signal, respectively, in response thereto;

(E) image displaying means for displaying an image of an anterior portion of the eye based on said anterior portion image signal from said light receiving means; and (F) calculating means for calculating a corneal configuration and an eye refractive power of the eye to be tested based on said cornea image signal and said retina image signal, respectively.

2. An ophthalmological measuring apparatus as claimed in claim 1, wherein said second optical path provides a path for said anterior portion reflected beam of light to said light receiving means to verify the alignment, said second optical path being commonly used for introducing said cornea reflected beam of light to said light receiving means.

3. An ophthalmological measuring apparatus as claimed in claim 1, wherein said first optical path of said eye refractive power measuring optical means comprises a first optical path composing means for introducing to the eye to be tested a fixation mark image for being gazed at by the eye from a fixation mark image projecting optical means for radiating the fixation mark image, an optical path diversifying means for introducing said corneal reflecting image to said corneal configuration measuring optical means, and a second optical path composing means for directing to said light receiving surface said cornea reflected image which has been introduced to said eye refractive power measuring optical means by said corneal configuration measuring optical means.

4. An ophthalmological measuring apparatus as claimed in claim 1, wherein said image displaying means displays a calculated result of said calculating means.

* * * * *